US007393872B2

(12) United States Patent
Lan

(10) Patent No.: US 7,393,872 B2
(45) Date of Patent: Jul. 1, 2008

(54) SODIUM CHANNEL BLOCKER COMPOSITIONS AND THE USE THEREOF

(75) Inventor: Nancy C Lan, Altadena, CA (US)

(73) Assignee: Euro-Celtique S.A., Luxembourg (LU)

( * ) Notice: Subject to any disclaimer, the term of this patent is extended or adjusted under 35 U.S.C. 154(b) by 231 days.

(21) Appl. No.: 10/644,783

(22) Filed: Aug. 21, 2003

(65) Prior Publication Data

US 2004/0054005 A1 Mar. 18, 2004

Related U.S. Application Data

(60) Division of application No. 09/971,007, filed on Oct. 5, 2001, which is a continuation of application No. PCT/US00/09387, filed on Apr. 10, 2000.

(60) Provisional application No. 60/128,543, filed on Apr. 9, 1999.

(51) Int. Cl.
*A61K 31/55* (2006.01)
*A61K 31/195* (2006.01)

(52) U.S. Cl. ..................................... 514/561; 514/217

(58) Field of Classification Search ................ 514/242, 514/269, 590, 812
See application file for complete search history.

(56) References Cited

U.S. PATENT DOCUMENTS

| 4,024,175 A | 5/1977 | Satzinger et al. |
|---|---|---|
| 4,087,544 A | 5/1978 | Satzinger et al. |
| 4,602,017 A | 7/1986 | Sawyer et al. |
| 4,894,476 A | 1/1990 | Butler et al. |
| 5,025,035 A | 6/1991 | Wallace |
| 5,179,109 A | 1/1993 | Kamenka et al. |
| 5,236,957 A | 8/1993 | Dostert et al. |
| 5,256,669 A | 10/1993 | Askanazi et al. |
| 5,330,515 A | 7/1994 | Rutecki et al. |
| 5,446,066 A | 8/1995 | Varasi et al. |
| 5,449,692 A | 9/1995 | Varasi et al. |
| 5,660,861 A | 8/1997 | Jao et al. |
| 5,712,277 A | 1/1998 | Nakamura-Craig et al. |
| 5,741,818 A | 4/1998 | Dimmock |
| 5,891,849 A | 4/1999 | Amstutz et al. |
| 5,905,069 A | 5/1999 | Borsook et al. |
| 5,942,510 A | 8/1999 | Floyd et al. |
| 6,113,915 A | 9/2000 | Aoki et al. |
| 6,180,624 B1 | 1/2001 | Hill |
| 6,187,338 B1 | 2/2001 | Caruso et al. |
| 6,207,685 B1 | 3/2001 | Lallement et al. |
| 6,242,488 B1 | 6/2001 | Bueno et al. |
| 6,281,211 B1 | 8/2001 | Cai et al. |
| 6,290,986 B1 | 9/2001 | Murdock et al. |
| 6,326,374 B1 | 12/2001 | Magnus et al. |
| 6,326,385 B1 | 12/2001 | Wickenden et al. |

FOREIGN PATENT DOCUMENTS

| DE | 198 02 327 A1 | 7/1999 |
|---|---|---|
| EP | 1 083 164 | 3/2001 |
| FR | 2 756 738 | 6/1998 |
| WO | WO 96/40628 | 12/1996 |
| WO | WO 97/05102 | 2/1997 |
| WO | WO 98/07447 | 2/1998 |
| WO | WO 98/08842 | 3/1998 |
| WO | WO 98/19674 A2 | 5/1998 |
| WO | WO 98/19674 A3 | 7/1998 |
| WO | WO 98/28255 | 7/1998 |
| WO | WO 98/43964 | 10/1998 |
| WO | WO 98/47869 | 10/1998 |
| WO | WO 99/12537 | 3/1999 |
| WO | WO 99/26614 | 6/1999 |
| WO | WO 99/37296 | 7/1999 |
| WO | WO 99/39712 | 8/1999 |
| WO | WO 99/44610 | 9/1999 |
| WO | WO 99/61408 | 12/1999 |
| WO | WO 00/02562 | 1/2000 |
| WO | WO 00/02592 | 1/2000 |
| WO | WO 00/57877 | 10/2000 |
| WO | WO 03/020273 A2 | 3/2003 |

OTHER PUBLICATIONS

"Trigeminal Neuralgia", www.enwikipedia.org, 2006.*
"About Post-Herpetic Neuralgia", www.aftershingles.com, 2000.*
"Herpes Zoster and Postherpetic Neuralgia", Mousey et al., American Family Physician, 2005, vol. 72. No. 6, pp. 1075-1080.*
"Postthepetic Neuralgia", Zagaria M.A., US Pharmacist, 2002, vol. 27, No. 10.*
"Treatment of Trigeminal Neuralgia at Mayo Clinic", www.mayoclinic.org. 2006.*
Backonja, M., et al., "Gabapentin for the Symptomatic Treatment of Painful Neuropathy in Patients With Diabetes Mellitus," *JAMA* 280:1831-1836, The American Medical Association (Dec. 1998).
Bennett, G.J., "Neuropathic Pain: An Overview," in *Molecular Neurobiology of Pain* 9:109-113, Borshook, D., ed., IASP Press, Seattle (1997).
Bensimon, G., et al., "A Controlled Trial of Riluzole in Amyotrophic Lateral Sclerosis," *New England J. Med.* 330:585-591, The Massachusetts Medical Society (1994).
Beydoun, A., "Postherpetic Neuralgia: Role of Gabapentin and Other Treatment Modalities," *Epilepsia* 40(*Suppl.* 6) :S51-S56, Lippincott Williams & Wilkins (Oct. 1999).
Blinder, B.J., et al., "Advances in Mood Stabilizing Medications," *West. J. Med.* 169:39-40, BMJ Publishing (1998).
Boyce, S., et al., "Selective NMDA NR2B antagonists induce antinociception without motor dysfunction: correlation with restricted localisation of NR2B subunit in dorsal horn," *Neuropharmacology* 38:611-623, Pergamon and Elsevier Science Ltd. (May 1999).

(Continued)

*Primary Examiner*—Brian Kwon
(74) *Attorney, Agent, or Firm*—Sterne, Kessler, Goldstein & Fox P.L.L.C.

(57) ABSTRACT

Methods of treating or preventing chronic pain or convulsion are disclosed by administering to an animal a sodium channel blocker and at least one of gabapentin and pregabalin. Also disclosed are pharmaceutical compositions and kits for the treatment or prevention of chronic pain or convulsion.

30 Claims, 2 Drawing Sheets

OTHER PUBLICATIONS

Brown, C.M., et al., "Neuroprotective properties of lifarizine compared with those of other agents in a mouse model of focal cerebral ischaemia," *British J. Pharmacol.* 115:1425-1432, Stockton Press (1995).

Bryans, J.S., and Wustrow, D.J., "3-Substituted GABA Analogs with Central Nervous System Activity: A Review," *Med. Res. Rev.* 19:149-177, John Wiley & Sons, Inc. (Mar. 1999).

Buchan, A.M., et al., "AMPA Antagonists: Do They Hold More Promise for Clinical Stroke Trials Than NMDA Antagonists?," *Supplement I, Stroke* 24:Il48-Il52, American Heart Association (1993).

Canavero, S., et al., "The riddle of trigeminal neuralgia," *Pain* 60:229-231, Elsevier Science B.V. (1995).

Carrazana, E.J., and Schachter, S.C., "Alternative uses of lamotrigine and gabapentin in the treatment of trigeminal neuralgia," *Neurology* 50:1192, The American Academy of Neurology (Apr. 1998).

Catterall, W.A., "Common modes of drug action on Na+ channels: local anesthetics, antiarrhythmics and anticonvulsants," *Trends Pharmacol. Sci.* 8:57-65, Elsevier Science Publishers B.V. (1987).

Catterall, W.A., "Neurotoxins That Act on Voltage-sensitive Sodium Channels on Excitable Membranes," *Ann. Rev. Pharmacol. Toxicol.* 20:15-43, Annual Reviews Inc. (1980).

Catterall, W.A., "Structure and Function of Voltage-Sensitive Ion Channels," *Science* 242:50-61, The American Association for the Advancement of the Science (1988).

Chapman, V., et al., "Effects of systemic carbamazepine and gabapentin on spinal neuronal responses in spinal nerve ligated rats," *Pain* 75:261-272, Elsevier Science B.V. (Apr. 1998).

Creveling, C.R., et al., "Batrachotoxin-Induced Depolarization and [$^3$H] Batrachotoxinin-A 20 α-Benzoate Binding in a Vesicular Preparation from Guinea Pig Cerebral Cortex," *Mol. Pharmacol.* 23:350-358, The American Society for Pharmacology and Experimental Therapeutics (1983).

Czuczwar, S.J., and Przesmycki, K., "Felbamate, Gabapentin and Topiramate as Adjuvant Antiepileptic Drugs in Experimental Models of Epilepsy," *Polish J. Pharmacol.* 53:65-68, Polish Academy of Sciences (2001).

De Sarro, G., et al., "Gabapentin Potentiates the Antiseizure Activity of Certain Anticonvulsants in DBA/2 Mice," *Eur. J. Pharmacol.* 349:179-185, Elsevier Science (1998).

Denicoff, K.D., et al., "Efficacy of Carbamazepine Compared With Other Agents: A Clinical Practice Survey," *J. Clin. Psychiatry* 55:70-76, Physicians Postgraduate Press, Inc. (1994).

Dichter, M.A., et al., "Drug Therapy: New Antiepileptic Drugs," *New Engl. J. Med.* 334:1583-1590, Massachusetts Medical Society (1996).

Field, M.J., et al., "Gabapentin and pregabalin, but not morphine and amitriptyline, block both static and dynamic components of mechanical allodynia induced by streptozocin in the rat," *Pain* 80:391-398, Elsevier Science B.V. (Mar. 1999).

Goldberg, I., and Green, B., "Focus on Gabapentin," *Focus* 8:1-6, Priory Lodge Education Ltd. (1997) from http://www.priory.com/focus8.htm.

Graham, S.H., et al., "A Dose-Response Study of Neuroprotection Using the AMPA Antagonist NBQX in Rat Focal Cerebral Ischemia," *J. Pharmacol. Exp. Therap.* 276:1-4, Williams & Wilkins (1996).

Graham, S.H., et al., "Neuroprotective Effects of a Use-Dependent Blocker of Voltage-Dependent Sodium Channels, BW619C89, in Rat Middle Cerebral Artery Occlusion," *J. Pharmacol. Exp. Therp.* 269:854-859, Williams & Wilkins (1994).

Gurney, et al., "Benefit of Vitamin E, Riluzole, and Gabapentin in a Transgenic Model of Familial Amyotrophic Lateral Sclerosis," *Ann. Neurol.* 39:147-157, The American Neurological Association (1996).

Hamill, O.P., et al., "Improved Patch-Clamp Techniques for High-Resolution Current Recording from Cells and Cell-Free Membrane Patches," *Pfluegers Arch* 391:85-100, Springer International (1981).

Hoekstra, M.S., et al., "Chemical Development of CI-1008, an Enantiomerically Pure Anticonvulsant," *Org. Process Res. Dev.* 1:26-38, American Chemical Society and Royal Society of Chemistry (1997).

Hunskaar, S., et al., "Formalin test in mice, a useful technique for evaluating mild analgesics," *J. Neurosci. Methods* 14:69-76, Elsevier Science Publishers B.V. (1985).

Iwasaki, Y., et al., "CNQX prevents spinal motor neuron death following sciatic nerve transection in newborn rats," *J. Neuro Sci.* 134:21-25, Elsevier Science B.V. (1995).

Kim, S.H., et al., "An experimental model for peripheral neuropathy produced by segmental spinal nerve ligation in the rat," *Pain* 50:355-363, Elsevier Science Publishers B.V. (1992).

Kingery, W.S., "A critical review of controlled clinical trials for peripheral neuropathic pain and complex regional pain syndromes," *Pain* 73:123-139, Elsevier Science B.V. (1997).

Kudoh, A., et al., "Effect of Carbamazepine on Pain Scores of Unipolar Depressed Patients with Chronic Pain: A Trial of Off-On-Off-On Design," *Clin. J. Pain* 14:61-65, Lippincott-Raven Publishers (1998).

Low, P.A., and Dotson, R.M., "Symptomatic Treatment of Painful Neuropathy," *JAMA* 280:1863-1864, The American Medical Association (Dec. 1998).

Lunardi, G., et al., "Clinical effectiveness of lamotrigine and plasma levels in essential and symptomatic trigeminal neuralgia," *Neurology* 48:1714-1717, Lippincott-Raven Publishers (1997).

Magnus, L., "Nonepileptic Uses of Gabapentin," *Epilepsia* 40 (Suppl 6):S66-S72, Lippincott Williams & Wilkins (Oct. 1999).

Nicholson, B., "Gabapentin use in neuropathic pain syndromes," *Dolor* 14:243-250, Publicaciones Permanyer (1999).

Ohizumi, Y., et al., "Specific Inhibitors of [$^3$H] Saxitoxin Binding to Skeletal Muscle Sodium Channels by Geographutoxin II, a Polypeptide Channel Blocker," *J. Biol. Chem.* 261:6149-6152, The American Society of Biological Chemists, Inc. (1986).

Rosenberg, J.M., et al., "The Effect of Gabapentin on Neuropathic Pain," *Clin. J. Pain* 13:251-255, Lippincott-Raven Publishers (1997).

Rosner, H., et al., "Gabapentin Adjunctive Therapy in Neuropathic Pain States," *Clin. J. Pain* 12:56-58, Lippincott-Raven Publishers (1996).

Rowbotham, M., et al., "Gabapentin for the Treatment of Postherpetic Neuralgia," *JAMA* 280:1837-1842, The American Medical Association (Dec. 1998).

Sheardown, M.J., et al., "AMPA, but not NMDA, receptor antagonism is neuroprotective in gerbil global ischaemia, even when delayed 24 h," *Eur. J. Pharmacol.* 236:347-353, Elsevier Science Publishers B.V. (1993).

Sist, T.C., et al., "Experience With Gabapentin for Neuropathic Pain in the Head and Neck: Report of Ten Cases," *Reg. Anesth.* 22:473-478, The American Society of Regional Anesthesia (1997).

Solaro, C., et al., "A patient with multiple sclerosis and Down's syndrome with a rare paroxysmal symptom at onset," *Eur. J. Neurol.* 6:505-507, Lippincott Williams & Wilkins (Jul. 1999).

Stys, P.K., et al., "Ionic Mechanisms of Anoxic Injury in Mammalian CNS White Matter: Role of $NA^+$ Channels and $Na^+-Ca^{2+}$ Exchanger," *J. Neurosci.* 12:430-439, Society of Neuroscience (1992).

Taylor, C.P., et al., "$Na^+$ channels as targets for neuroprotective drugs," *Trends Pharmacol. Sci.* 16:309-316, Elsevier Science Ltd. (1995).

Verdoorn, T.A., et al., "Functional Properties of Recombinant Rat $GABA_A$ Receptors Depend upon Subunit Composition," *Neuron* 4:919-928, Cell Press (1990).

Victor, M., et al., "Chapter 352: Diseases of the Cranial Nerves," in *Harrison's Principles of Internal Medicine* 11:2035-2040, Braunwald, et al., eds., McGraw-Hill Inc. (1987).

Wamil, A.W., and McLean, M.J., "Limitation by gabapentin of high frequency action potential firing by mouse central neurons in cell culture," *Epilepsy Res.* 17:1-11, Elsevier Science B.V. (1994).

Wrathall, J.R., et al., "Amelioration of Functional Deficits from Spinal Cord Trauma with Systemically Administered NBQX, an Antagonist of Non-N-methyl-D-aspartate receptors," *Exp. Neurology* 137:119-126, Academic Press, Inc. (1996).

Yoon, M.H., and Yaksh, T.L., "Evaluation of Interaction between Gabapentin and Ibuprofen on the Formalin Test in Rats," *Anesthesiology* 91:1006-1013, Lippincott Williams & Wilkins, Inc. (Oct. 1999).

Dialog File 351, Accession No. 12613976, Derwent WPI English language abstract for DE 198 02 327 A1 (Document AN3).

List of abstracts concerning SCRIP 1773:14 (1992) provided by client.

List of abstracts concerning SCRIP 1870:8 (1993) provided by client.

STN Database, Accession No. 1998:9096, "Warner-Lambert forecasts 35% earnings growth," SCRIP 2330:8 (1998).

U.S. Appl. No. 60/126,553, Hogenkamp et al., filed Mar. 26, 1999.

Attal, N., "Antiepileptic drugs in the treatment of neuropathic pain," *Exp. Rev. Neurotherapeutics* 1:199-206, Future Drugs Ltd. (2001).

Bennett, G.J., "Neuropathic Pain: New Insights, New Interventions," *Hospital Practice* 33:95-98, 101-104, 107-110, 113-114, The McGraw-Hill Companies, Inc. (1998).

Borowicz, K.K., et al., "Effect of Gabapentin on the Anticonvulsant Activity of Antiepileptic Drugs against Electroconvulsions in Mice: An Isobolographic Analysis," *Epilepsia* 43:956-963, Blackwell Publishing, Inc. (2002).

\* cited by examiner

SODIUM CHANNEL BLOCKER COMPOSITIONS AND THE USE THEREOF

The present application is a divisional of application Ser. No. 09/971,007, filed Oct. 5, 2001, which is a continuation of International Application PCT/US00/09387, published under PCT Article 21(2) in English as WO 00/61188 on Oct. 19, 2000, having an International filing date of Apr. 10, 2000, and which claims the benefit under 35 U.S.C. § 119(e) to U.S. Provisional Application No. 60/128,543, filed Apr. 9, 1999. The full disclosure of each of these applications is herein incorporated by reference.

BACKGROUND OF THE INVENTION

1. Field of the Invention

This invention is in the field of medicinal chemistry. In particular, the invention relates to compositions comprising blockers of sodium ($Na^+$) channels and at least one of gabapentin or pregabalin. The invention also relates to methods for the treatment of chronic pain or convulsions comprising coadministering a sodium channel blocker and at least one of gabapentin or pregabalin.

2. Related Background Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., Trends Pharmacol. Sci. 8:57-65 (1987)). Each of these agents is believed to act by interfering with the rapid influx of $Na^+$ ions. Recently, other $Na^+$ channel blockers such as BW619C89 and lifarizine have been shown to be neuroprotective in animal models of global and focal ischemia and are presently in clinical trials (Graham et al., J. Pharmacol. Exp. Ther. 269:854-859 (1994); Brown et al., British J. Pharmacol. 115:1425-1432 (1995); SCRIP 1870:8 (1993); SCRIP 1773:14 (1992)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., J. Neurosci. 12:430-439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., New Engl. J. Med. 330:585-591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, Trends Pharmacol. Sci. 16:309-316 (1995)), and carbamazepine and lamotrigine have been used for the treatment of manic depression (Denicott et al., J. Clin. Psychiatry 55: 70-76 (1994)).

It has been established that there are at least five to six sites on the voltage-sensitive $Na^+$ channels which bind neurotoxins specifically (Catterall, W. A., Science 242:50-61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., Ann. Rev. Pharmacol. Toxicol. 10:15-43 (1980)).

Chronic pain or neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia and reflex sympathetic dystrophy and lower back pain. The chronic pain is different from acute pain in that patients suffer the abnormal pain sensations that can be described as spontaneous pain, continuous superficial burning and/or a deep aching pain. The pain can be evoked by heat-, cold- and mechano-hyperalgesia or by heat-, cold- and mechano-allodynia (International association for the study of pain: The classification of chronic pain (1995); Bennett G. J. Molecular Neurobiology of Pain, Progress in Pain Research and Management Vol. 9, pp. 109-113, edited by D. Borsook, 1997). In most cases, chronic neuropathic pain responds poorly to treatment with opiates or nonsteroidal anti-inflammatory analgesia.

Carbamazepine (Tegretol™), a sodium channel blocker anticonvulsant, has been shown to be effective in trigeminal neuralgia. However, one third of patients cannot tolerate the drug in the dose required to alleviate the pain (Victor et al., Harrison's Principles of Internal Medicine. $11^{th}$ ed. New York: McGraw-Hill 1987; 2035-40). In addition, carbamazepine may cause aplastic anemia, agranulocytosis, and hypersensitivity reaction (Canavero et al., Pain 60:229-31 (1995)). These serious side effects are dose related. Carbamazepine is the only drug approved by the FDA for this indication.

There are no other drugs thus far that have been approved for chronic pain. Lamotrigine (Lamictal) is a sodium channel blocker that has been approved by the FDA for treating convulsions. This drug has also been shown to be effective for treating chronic pain (Lundardi et al., Neurology 48: 1714 (1997)). However, the doses required for the treatment of chronic pain are relatively high and result in side effects. The major side effect of this drug is severe, potentially life-threatening rashes (Dichter and Brodie, New Engl. J. Med. 334: 1583 (1996)).

Gabapentin (Neurontin™), an anticonvulsant with unknown mechanism of action has been shown recently to be efficacious for treating chronic pain (Rowbotham et al., JAMA 280: 1837-1842 (1998) and Backonja et al., JAMA 280: 1831-1836 (1998)). However, higher doses are necessary to treat chronic pain. Side effects such as exacerbated absence seizures and nausea are associated with these high doses in addition to being fetotoxic. In addition, in clinical trials, gabapentin showed limited efficacy (i.e., less than 50% of patient population showed effectiveness, whereas 15-20% of patients treated with placebo showed effectiveness).

Pregabalin is a potent follow-up compound to gabapentin. The compound has similar activity to gabapentin and is currently under clinical trials for neuropathic pain (SCRIP 2330:8 (1998)).

Thus, a need exists for treatments of chronic pain and convulsions that avoid the side effects exhibited by lamotrigine, carbamazepine and gabapentin. The present invention provides compositions and methods which reduces such side effects and improves the response rate of patients.

SUMMARY OF THE INVENTION

The present invention relates to pharmaceutical compositions, comprising a first agent which is a sodium channel blocker, and a second agent selected from the group consisting of gabapentin, pregabalin, salts thereof and combinations thereof; wherein the total amount of said first agent and said second agent is effective to treat, prevent or ameliorate chronic pain or convulsions. Preferably, said first agent and said second agent are present in synergistic amounts, that is the sodium channel blocker and at least one of gabapentin or pregabalin or their salts are present in amounts lower than those used to treat or prevent chronic pain or convulsions when used alone. The invention further relates to such compositions that further comprise a pharmaceutically acceptable carrier, and optionally include pharmaceutically acceptable excipients.

The invention also relates to a method of treating, preventing or ameliorating chronic pain or convulsions, comprising administering to a patient in need thereof a first agent which is a sodium channel blocker, and a second agent selected from the group consisting of gabapentin, pregabalin, salts thereof and combinations thereof; wherein the total amount of said first agent and said second agent is effective to treat, prevent or ameliorate chronic pain or convulsions. Preferably, said sodium channel blocker and at least one of gabapentin and pregabalin are administered in synergistic amounts. Preferably, the two agents are administered substantially simultaneously as defined herein. The sodium channel blocker and at least one of gabapentin and pregabalin may be administered separately or as part of a single pharmaceutical composition.

The invention also relates to a kit for the treatment of chronic pain or convulsions comprising a carrier containing one or more containers one of which comprises a sodium channel blocker and another of which comprises an agent selected from the group consisting of gabapentin, pregabalin, salts thereof and combinations thereof.

DESCRIPTION OF THE FIGURE

FIG. 1A: IV-curves, FIG. 1C: steady-state inactivation, FIG. 1B: repriming kinetics, and FIG. 1D: time course of binding.

DETAILED DESCRIPTION OF THE INVENTION

Figure 1A:
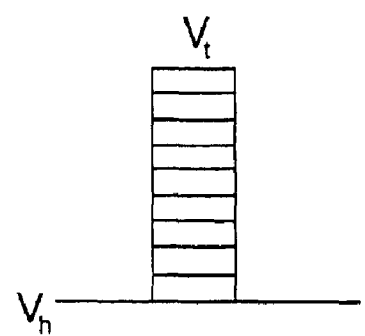
FIGS. 1A, 1B, 1C, and 1D are voltage pulse protocols used to assess the potency and kinetics of inhibition of the $Na^+$ channels by the compounds as follows.
Figure 1B:
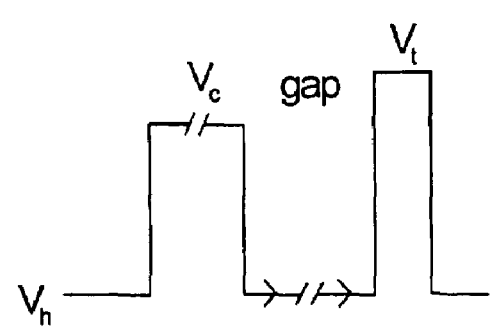
Figure 1C:
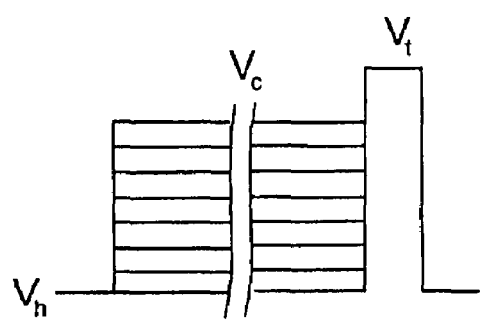
Figure 1D:
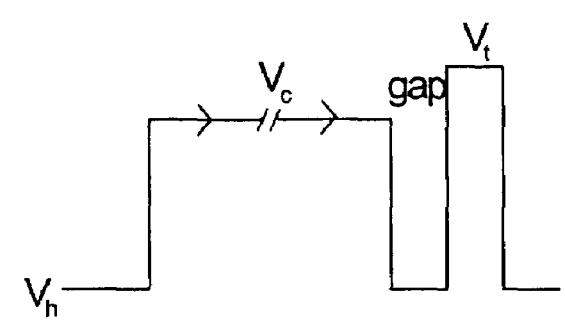

The present invention arises out of the discovery that administration of a sodium channel blocker with gabapentin, pregabalin, salts thereof or combinations thereof, is effective for the treatment, prevention and/or amelioration of chronic pain and convulsions. The present invention also arises out of the discovery that it is possible to treat, prevent and/or ameliorate chronic pain and convulsions with synergistic amounts of at least one sodium channel blocker together with gabapentin, pregabalin or salts thereof or combinations thereof.

Useful first agents and second agents are described in the sections below. The first agent can be a single sodium channel blocker, or can two or more sodium channel blockers. Likewise, the second agent can be a single compound or can be a mixture of two or more compounds.

The present invention relates to pharmaceutical compositions, comprising a first agent which is a sodium channel blocker, and a second agent selected from the group consisting of gabapentin, pregabalin, salts thereof and combinations thereof; wherein the total amount of said first agent and said second agent is effective to treat, prevent or ameliorate chronic pain or convulsions. Preferably, said first agent and said second agent act in synergy to treat, prevent or ameliorate chronic pain or convulsions. The invention further relates to such compositions that further comprise a pharmaceutically acceptable carrier, and optionally include pharmaceutically acceptable excipients.

The invention also relates to a method of treating, preventing or ameliorating chronic pain or convulsions, comprising administering to a patient in need thereof a first agent which is a sodium channel blocker, and a second agent selected from the group consisting of gabapentin, pregabalin, salts thereof and combinations thereof; wherein the total amount of said first agent and said second agent is effective to treat, prevent or ameliorate chronic pain or convulsions. Preferably, said sodium channel blocker and at least one of gabapentin and pregabalin are administered in synergistic amounts. Preferably the agents are administered substantially simultaneously. The sodium channel blocker and at least one of gabapentin and pregabalin may be administered separately or as part of a single pharmaceutical composition in the treatment of pain, especially for treatment of chronic pain disorders. Such disorders include, but are not limited to, inflammatory pain, postoperative pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgic, neuropathic, and idiopathic pain syndromes.

Thus, one aspect of the present invention is a method for the treatment of pain as listed above. Pain such as inflammatory pain, neuropathic pain, cancer pain, postoperative pain, and idiopathic pain which is pain of unknown origin, for example, phantom limb pain are included especially. Neuropathic pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain from which diabetics suffer.

Another aspect of the invention is directed to a method for treating convulsions as described above.

Gabapentin and Pregabalin

One agent employed in the composition and methods of the present invention (referred to as the second agent) is a derivative of GABA (4-aminobutanoic acid). Gabapentin is a generic term used to identify the compound 1-(aminomethyl) cyclohexaneacetic acid. The compound can also exist as a hydrate, and the compound can exist in an amorphous or crystalline form. For example, U.S. Pat. No. 4,894,476 discloses crystalline gabapentin monohydrate and a method for making it. PCT Published Application No. WO99/61408 discloses a non-hydrated gabapentin polymorph. PCT Published Application No. 98/28255 discloses alternate crystal forms of gabapentin (form II and form III) and methods for making these forms. Gabapentin is useful in the present invention in all of its forms. Preferred forms include those forms described in U.S. Pat. Nos. 4,024,175, 4,087,544 and 4,894,476. Gabapentin can also form salts, for example a hydrochloride salt. Salts of gabapentin are included within the scope of the invention.

Pregabalin is a generic term used to identify the compound 3-(aminomethyl)-5-methylhexanoic acid. This compound has a stereocenter and the 3S-enantiomer, (3S)-3-(aminomethyl)-5-methylhexanoic acid is the more active stereoisomer. Racemic mixtures or mixtures having an enantiomeric excess of the 3S stereoisomer are preferred for the present invention. The compound is useful in the present invention in all of its forms, whether amorphous or crystalline, anhydrous or hydrated. Pregabalin can also exist in salt forms, which are included within the scope of the invention.

Gabapentin and pregabalin can be formulated to provide greater stability to the compound. Useful excipients for inclusion with gabapentin and pregabalin include neutral amino acids, such as glycine and L-valine; and humectants, such as ethylene glycol, propylene glycol and glycerine. The active compounds may also be coated as agglomerated powders with a polymer such as polyvinyl pyrrolidone to provide better stability and processing characteristics.

Sodium Channel Blockers

The first agent in the compositions and methods of the present invention is a sodium channel blocker.

Compounds can be tested for their Na+ channel blocking activity by the electrophysiological and binding assays which are described herein. Preferred sodium channel blocking properties exhibit an Ki of about 100 μM or less in the electrophysiological assay. Preferably, the sodium channel blockers exhibit an Ki of 10 μM or less. Most preferably, the sodium channel blockers exhibit an Ki of about 1.0 μM or less.

Sodium channel blockers that may be used in the practice of the invention include any of the known sodium channel blockers as described herein, including compounds disclosed in the following documents.

PCT International Published Application WO96/40628 discloses semicarbazones represented by Formula I:

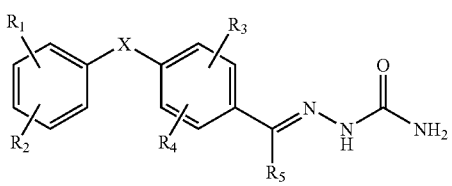

where $R_1$-$R_4$ are independently hydrogen, halogen, $C_{1-9}$ alkyl, $C_{3-9}$ cycloalkyl, cyano, $C_{1-9}$ alkoxy, or $C_{6-10}$ aryloxy; $R_5$ is hydrogen, $C_{1-9}$ alkyl, $C_{3-9}$ cycloalkyl, or $C_{6-10}$ aryl; and X is oxygen or sulfur. The compounds are disclosed to be useful as anticonvulsants.

PCT International Published Application WO98/47869 discloses the compounds claimed in WO 96/40628 act as sodium channel blockers. In addition, it discloses sodium channel blocking semicarbazones and thiosemicarbazones represented by Formula II:

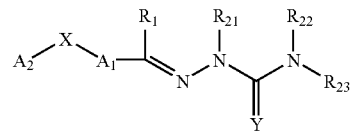

or a pharmaceutically acceptable salt or prodrug thereof, wherein:

Y is oxygen or sulfur;

$R_1$ is hydrogen, alkyl, cycloalkyl, alkenyl, alkynyl, haloalkyl, aryl, aminoalkyl, hydroxyalkyl, alkoxyalkyl or carboxyalkyl;

$R_{21}$, $R_{22}$ and $R_{23}$ are independently hydrogen, alkyl, cycloalkyl, alkenyl, alkynyl, haloalkyl, aryl, aminoalkyl, hydroxyalkyl, alkoxyalkyl or carboxyalkyl, or $R_{21}$, is defined as above, and $R_{22}$ and $R_{23}$ together with the nitrogen atom to which they are attached form a heterocycle, including piperidine, piperazine, or morpholine;

$A_1$ and $A_2$ are independently aryl, heteroaryl, saturated or partially unsaturated carbocycle or saturated or partially unsaturated heterocycle, any of which is optionally substituted;

X is one or O, S, $NR_{24}$, $CR_{25}R_{26}$, C(O), $NR_{24}C(O)$, C(O)$NR_{24}$, SO, $SO_2$ or a covalent bond; where $R_{24}$ is hydrogen, alkyl, cycloalkyl, alkenyl, alkynyl, haloalkyl, aryl, aminoalkyl, hydroxyalkyl, alkoxyalkyl or carboxyalkyl; and $R_{25}$ and $R_{26}$ are independently hydrogen, alkyl, cycloalkyl, alkenyl, alkynyl, haloalkyl, aryl, aminoalkyl, hydroxyalkyl, alkoxyalkyl or carboxyalkyl.

**PCT International Published Application WO99/26614 (Appl. No. PCT/US98/24965, filed Nov. 20, 1998), discloses sodium channel blockers represented by Formula III:

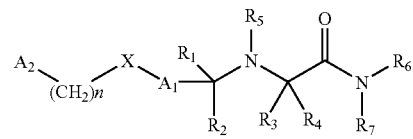

or a pharmaceutically acceptable salt or prodrug thereof, wherein:

$R_1$ $R_2$, $R_3$ and $R_4$ are independently hydrogen, alkyl, cycloalkyl, alkenyl, alkynyl, haloalkyl, aryl, aminoalkyl, hydroxyalkyl, alkoxyalkyl or carboxyalkyl;

$R_5$, $R_6$ and $R_7$ are independently hydrogen, alkyl, cycloalkyl, alkenyl, alkynyl, haloalkyl, aryl, aminoalkyl, hydroxyalkyl, alkoxyalkyl or carboxyalkyl, or $R_5$, is defined as above, and $R_6$ and $R_7$ together with the nitrogen atom to which they are attached form a heterocycle;

$A_1$ and $A_2$ are independently aryl, heteroaryl, saturated or partially unsaturated carbocycle or saturated or partially unsaturated heterocycle, any of which is optionally substituted;

X is one or O, S, $NR_8$, $CH_2$, C(O), $NR_8C(O)$, C(O)$NR_8$, SO, $SO_2$ or a covalent bond; where $R_8$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3.

**PCT International Published Application WO 99/39712 (Appl. No. PCT/US99/02419, filed Feb. 4, 1999), discloses sodium channel blockers represented by Formula IV:

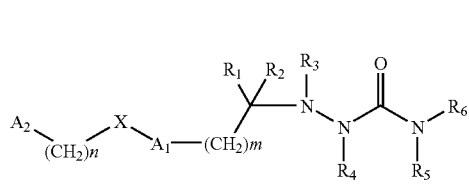

or a pharmaceutically acceptable salt or prodrug thereof, wherein:

$R_1$ and $R_2$ are independently hydrogen, alkyl, cycloalkyl, alkenyl, alkynyl, haloalkyl, aryl, aminoalkyl, hydroxyalkyl, alkoxyalkyl or carboxyalkyl;

$R_3$, $R_4$, $R_5$ and $R_6$ are independently hydrogen, alkyl, cycloalkyl, alkenyl, alkynyl, haloalkyl, aryl, aminoalkyl, hydroxyalkyl, alkoxyalkyl or carboxyalkyl, or $R_3$ and $R_4$ is defined as above, and $R_5$ and $R_6$ together with the nitrogen atom to which they are attached form a heterocycle, including piperidine, piperazine, morpholine;

$A_1$ and $A_2$ are independently aryl, heteroaryl, saturated or partially unsaturated carbocycle or saturated or partially unsaturated heterocycle, any of which is optionally substituted;

X is one of O, S, $NR_7$, $CH_2$, C(O), $NR_7C(O)$, $C(O)NR_7$, SO, $SO_2$ or a covalent bond; where $R_7$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3.

m is 0, 1, 2, or 3.

PCT International Published Application WO98/08842 discloses sodium channel blockers having the Formula V:

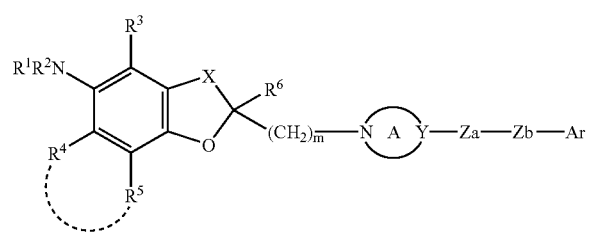

wherein $R^1$ and $R^2$ each represents hydrogen, lower alkyl which may be substituted or acyl; $R^3$, $R^4$ and $R^5$ each represents lower alkyl which may be substituted or lower alkoxy which may be substituted or $R^4$ or $R^5$ taken together represent a 5- or 6-membered carbocyclic group; $R^6$ represents lower alkyl; Ar represents an aromatic group which may be substituted; ring A represents a 5- to 8-membered nitrogen-containing heterocyclic ring which may be substituted; X represents lower alkylene which may be substituted; Y represents carbon or nitrogen; Za represents $CH_2$, $COCH_2$, $OCH_2$, $SCH_2$, $NHCH_2$, etc.; Zb represents a bond or a divalent aliphatic hydrocarbon group which may be substituted and may contain O, N or S; and m represents an integer of 1 to 3, or a salt thereof.

U.S. Pat. No. 5,449,692 discloses compounds having Formula VI:

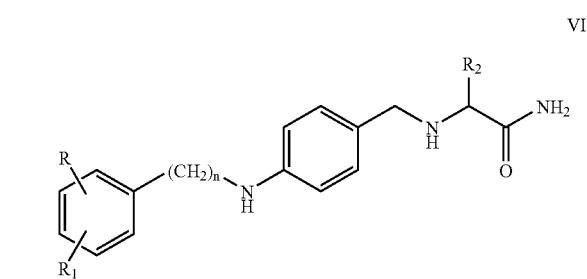

wherein n is an integer of 1 to 4; each of R and $R_1$, which may be the same or different, is hydrogen, halogen, trifluoromethyl or $C_1$-$C_4$ alkoxy; $R_2$ is hydrogen or $C_1$-$C_4$ alkyl; and a pharmaceutically acceptable salts thereof; and wherein when, at the same time, R is hydrogen, $R_1$ is hydrogen or halogen and n is one, then $R_2$ is other than hydrogen or methyl; and of Formula VIa:

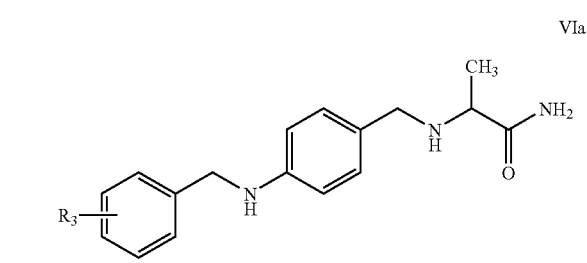

wherein $R_3$ is halogen, and a pharmaceutical acceptable salt thereof.

Other sodium channel blocker compounds useful in the practice of the invention include compounds disclosed in PCT International Published Application WO 97/05102 having Formula VII:

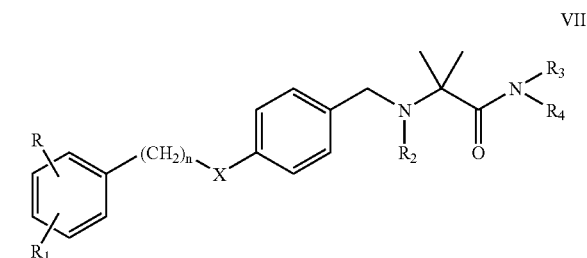

wherein n is zero, 1, 2 or 3; X is —O—, —S—, —$CH_2$— or —NH—; each of R and $R_1$ independently is hydrogen, $C_1$-$C_6$ alkyl, halogen, hydroxy, $C_1$-$C_4$ alkoxy or trifluoromethyl; each of $R_2$, $R_3$ and $R_4$ independently is hydrogen, $C_1$-$C_6$ alkyl or $C_3$-$C_7$ cycloalkyl; and the pharmaceutically acceptable salts thereof.

Other sodium channel blocker compounds useful in the practice of the invention, include compounds disclosed in U.S. Pat. No. 5,446,066 having Formula VIII:

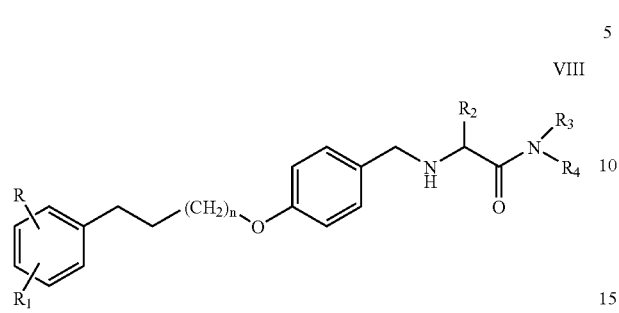

wherein n is zero or an integer of 1 to 3; each of R and $R_1$, which may be the same or different, is hydrogen, halogen, trifluoromethyl or $C_1$-$C_4$ alkoxy; $R_2$ is hydrogen or $C_1$-$C_4$ alkyl optionally substituted by hydroxy; each of $R_3$ and $R_4$ independently is hydrogen or $C_1$-$C_4$ alkyl; or a pharmaceutically acceptable salt thereof; and of Formula VIIIa:

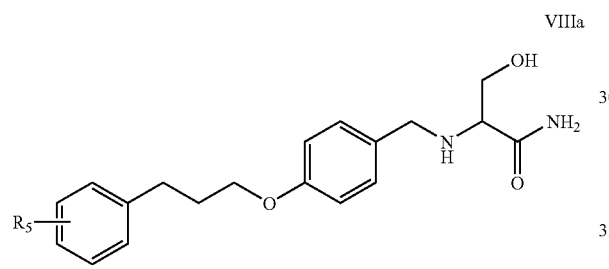

wherein $R_5$ is hydrogen, halogen, trifluoromethyl or $C_1$-$C_4$ alkoxy, or a pharmaceutically acceptable salt thereof.

Other sodium channel blocker compounds useful in the practice of the invention include compounds disclosed in U.S. Pat. No. 5,236,957 having Formula IX:

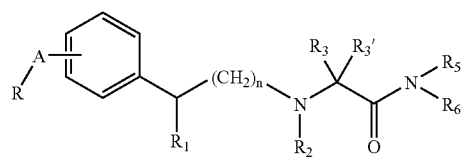

wherein R is $C_1$-$C_8$ alkyl, $C_3$-$C_8$ cycloalkyl, furyl, thienyl, pyridyl or unsubstituted or substituted phenyl; A is a —$(CH_2)_m$— or —$(CH_2)_p$—X—$(CH_2)_q$— group wherein X is —O—, —S— or —$NR_4$—; $R_1$, $R_2$, $R_3$, and $R'_3$ are hydrogen or $C_1$-$C_6$ alkyl, n, m, p, and q are zero or an integer from 1 to 3; and each of $R_5$ and $R_6$ is independently hydrogen or $C_1$-$C_6$ alkyl, and the pharmaceutical acceptable salts thereof.

Other sodium channel blocker compounds useful in the practice of the invention include compounds disclosed in PCT International Published Application WO 98/43964 having Formula X:

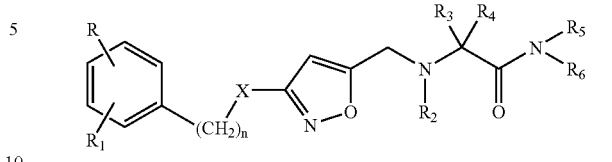

wherein n is zero, or an integer of 1 to 3; X is O, S or NH; each of R and $R_1$, which are the same or different, is hydrogen, $C_1$-$C_6$ alkyl, halogen, hydroxy, $C_1$-$C_4$ alkoxy or trifluoromethyl; each of $R_2$, $R_5$ and $R_6$, which are the same or different, is hydrogen or $C_1$-$C_6$ alkyl; each of $R_3$ and $R_4$, which are the same or different, is hydrogen or $C_1$-$C_6$ alkyl or $R_3$ or $R_4$ taken together with the adjacent carbon atom form a $C_3$-$C_7$ cycloalkyl ring; and their pharmaceutically acceptable salts.

Other sodium channel blocker compounds may be used in the practice of the invention, including compounds disclosed in U.S. patent application Ser. No. 60/126,553 having Formula XI and XII:

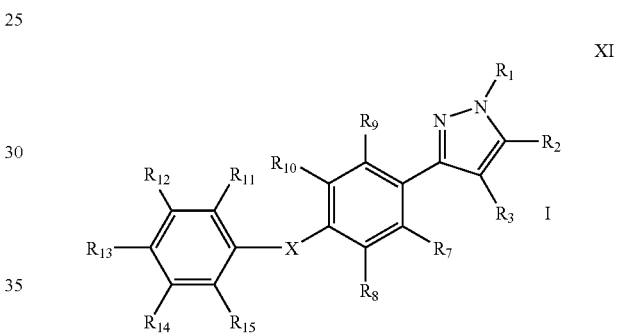

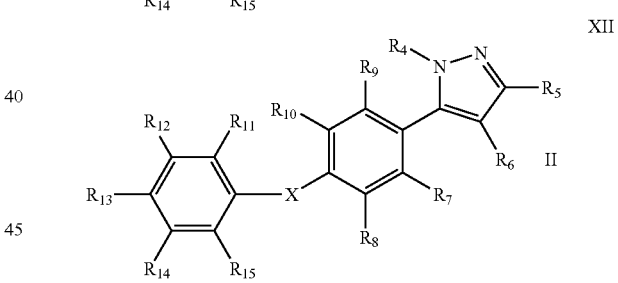

or a pharmaceutically acceptable salt, prodrug or solvate thereof, wherein:

$R_1$ and $R_4$ are independently selected from the group consisting of hydrogen, alkyl, cycloalkyl, aryl, aralkyl, $C(O)R_{16}$, $S(O)R_{16}$, $SO_2R_{16}$ all of which may be optionally substituted;

$R_2$, $R_3$, $R_5$ and $R_6$ are independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl or carboxyalkyl, or taken together with the carbon atoms to which they are attached to form a carbocycle or heterocycle. Examples of bridges formed by $R_2$ and $R_3$ or $R_5$ and $R_6$ taken together are —$OCH_2O$—, —$OCF_2O$—, —$(CH_2)_3$—, —$(CH_2)_4$—, —$OCH_2CH_2O$—, —$CH_2N(R_{17})CH_2$—, —$CH_2CH_2N(R_{17})CH_2$—, —$CH_2N(R_{17})CH_2CH_2$— and —CH=CH—CH=CH—; where $R_{17}$ is hydrogen, alkyl, cycloalkyl;

$R_7$, $R_8$, $R_9$, $R_{10}$, $R_{11}$, $R_{12}$, $R_{13}$, $R_{14}$, and $R_{15}$ are independently selected from the group consisting of hydrogen, halo, haloalkyl, aryl, cycloalkyl, saturated or partially unsaturated heterocycle, heteroaryl, alkyl, alkenyl, alkynyl, arylalkyl, arylalkenyl, arylalkenyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamido, hydroxy, thiol, acyloxy, azido, alkoxy, carboxy, carbonylamido or alkylthiol; or $R_{11}$ and $R_{12}$ or $R_{12}$ and $R_{13}$ are taken together with the carbon atoms to which they are attached to form a carbocycle or heterocycle. Examples of bridges formed by $R_{11}$ and $R_{12}$ or $R_{12}$ and $R_{13}$ taken together are —OCH$_2$O—, —OCF$_2$O—, —(CH$_2$)$_3$—, —(CH$_2$)$_4$—, —OCH$_2$CH$_2$O—, —CH$_2$N(R$_{17}$)CH$_2$—, —CH$_2$CH$_2$N(R$_{17}$)CH$_2$—, —CH$_2$N(R$_{17}$)CH$_2$CH$_2$— and —CH=CH—CH=CH—; where $R_{17}$ is defined as above;

$R_{16}$ is selected from the group consisting of amino, alkyl, cycloalkyl, aralkyl, aryl, or heteroaryl;

X is one of O, S, NR$_{17}$, CH$_2$, C(O), NR$_{17}$C(O), C(O)NR$_{17}$, SO, SO$_2$, or a covalent bond where $R_{17}$ is defined as above.

Exemplary compounds that may be employed as blockers of sodium channels in the compositions and methods of the present invention include, without limitation:

Lidocaine;
Tetracaine;
Phenytoin;
Carbamazepine;
Lamotrigine;
5-(2,3,5-trichlorophenyl)-2,4-diamino-pyrimidine (BW1003C87);
4-amino-2-(4-methylpiperazine-1-yl)-5-(2,3,5-trichlorophenyl)pyrimidine (BW619C89);
Zonisamide;
Riluzole;
Lifarizine;
(=)-cis-3,4-dichloro-N-methyl-N-[2-(1-pyrrolidinyl)-cyclohexyl]-benzamide (U54494A);
N-[3-(2,6-dimethyl-1-piperidinyl)]-α-phenylbenzeneacetamide (PD85639);
Ralitoline;
N-(2-chloro-6-methylphenyl)-N-4-pyridinyl urea (CI953);
Fluarizine;
Verapamil;
Carvedilol;
N-acenaphth-5-yl-N'-4-methoxynaphthyl guanidine CNS 1237;
Mexiletine;
Amitriptyline;
1-(4-(4-fluorophenoxy)benzyl)semicarbazide;
5-methylthio-3-(4-phenoxyphenyl)-1H-pyrazole-1-carboxamide;
5-methylsulfinyl-3-(4-phenoxyphenyl)-1H-pyrazole-1-carboxamide;
3-[4-(4-fluorophenoxy)phenyl]-1H-pyrazole-1-carboxamide;
3-[4-(4-nitrophenoxy)phenyl]-1H-pyrazole-1-carboxamide;
3-[4-(4-methoxyphenoxy)phenyl]-1H-pyrazole-1-carboxamide;
3-[4-(3-chloro-2-cyanophenoxy)phenyl]-1H-pyrazole-1-carboxamide;
3-[4-(2,4-difluorophenoxy)phenyl]-1H-pyrazole-1-carboxamide;
3-[4-(2-chloro-4-fluorophenoxy)phenyl]-1H-pyrazole-1-carboxamide;
1-[3-[4-(4-nitrophenoxy)phenyl]-1H-pyrazole ]ethanone;
2-methyl-1-[3-(4-phenoxyphenyl)-1H-pyrazole]propanone;
3-[4-(4-fluorophenoxy)phenyl]-2H-pyrazole-2-carboxamide;
1-methanesulfonyl-3-(4-phenoxy)phenyl-1H-pyrazole;
1-(4-phenoxybenzyl)semicarbazide;
1-(4-(4-fluorophenoxy)benzyl)semicarbazide;
1-(4-(4-chlorophenoxy)benzyl)semicarbazide;
1-(4-(4-bromophenoxy)benzyl)semicarbazide;
1-(4-(4-methoxyphenoxy)benzyl)semicarbazide;
1-(4-(4-trifluoromethylphenoxy)benzyl)semicarbazide;
1-(4-(4-methylphenoxy)benzyl)semicarbazide;
1-(4-(3,4-difluorophenoxy)benzyl)semicarbazide;
1-(4-(4-chloro-2-fluorophenoxy)benzyl)semicarbazide;
1-(4-(4-nitrophenoxy)benzyl)semicarbazide;
1-(4-(3-methylphenoxy)benzyl)semicarbazide;
1-(4-(4-t-butylphenoxy)benzyl)semicarbazide;
1-(4-(4-propylphenoxy)benzyl)semicarbazide;
1-(4-(4-s-butylphenoxy)benzyl)se niicarbazide;
1-(4-(3 ,4-methylenedioxyphenoxy)benzyl)semicarbazide;
1-(4-cyclohexyloxybenzyl)semicarbazide;
1-(4-cycloheptyloxybenzyl)semicarbazide;
1-(4-(5-indanyloxy)benzyl)semicarbazide;
1-(4-(6-quinolinyloxy)benzyl)semicarbazide;
1-(4-(4-fluorophenoxy)-3-fluorobenzyl)semicarbazide;
1-(4-(tetrahydropyranyloxy)benzyl)semicarbazide;
1-(4-(4-fluorophenoxy)benzyl-4-methylsemicarbazide;
1-(4-(4-fluorophenoxy)benzyl)-2-methylsemicarbazide;
2-(4-(2-fluorobenzyloxy)benzylamino)-2-methyl-propanamide;
2-(4-(4-fluorophenoxy)benzylamino)-2-methyl-propanamide;
2-(4-(3,4-methylenedioxyphenoxy)benzylamino)-2-methyl-propanamide;
2-(4-(3,4-methylenedioxybenzyloxy)benzylamino)-2-methyl-propanamide;
2-(4-cyclohexyloxybenzylamino)-2-methyl-propanamide;
2-(4-(5,6,7,8-tetrahydro-2-naphthoxy)benzylamino)-2-methyl-propanamide;
2-(4-(2-adamantanoxy)benzylamino)-2-methyl-propanamide;
2-(4-(4-Chloro-2-fluorophenoxy)benzylamino)-2-methyl-propanamide;
2-(4-(2,4-difluorophenoxy)benzylamino)-2-methyl-propanamide;
2-(4-(3,4-difluorophenoxy)benzylamino)-2-methyl-propanamide;
2-(4-(6-bromo-4-fluorophenoxy)benzylamino)-2-methyl-propanamide;
2-(4-(4-nitrophenoxy)benzylamino)-2-methyl-propanamide;
2-(4-(4-tetrahydropyranoxy)benzylamino)-2-methyl-propanamide;
2-(4-(3,5-difluorophenoxy)benzylamino)-2-methyl-propanamide;
2-(4-(4-chlorophenoxy)benzylamino)-2-methyl-propanamide;
2-(4-(4-methylphenoxy)benzylamino)-2-methyl-propanamide;
2-(4-(2-chloro-4-fluorophenoxy)benzylamino)-2-methyl-propanamide;
2-(4-(5-indanoxy)benzylamino)-2-methyl-propanamide;
2-(4-cycloheptoxybenzylamino)-2-methyl-propanamide;
2-(4-(1-methyl-4-piperidinoxy)benzylamino)-2-methyl-propanamide;

2-(4-(exo-2-norbornoxy)benzylamino)-2-methyl-propanamide;

2-(3-(4-fluorophenoxy)-5-pyridylmethylamino)-2-methyl-propanamide;

2-(4-(4-pyridinoxy)benzylamino)-2-methyl-propanamide;

2-(3-fluoro-4-(4-fluorophenyl)benzylamino)-2-methyl-propanamide;

2-(4-(2-pyrimidinoxy)benzylamino)-2-methyl-propanamide;

2-(4-(6-quinolinoxy)benzylamino)-2-methyl-propanamide;

2-(4-(N,N-diphenylamino)benzylamino)-2-methyl-propanamide;

2-(4-diphenylmethoxy)benzylamino-2-methyl-propanamide; and 2-(4-triphenylmethoxy)benzylamino-2-methyl-propanamide;

or pharmaceutically acceptable salts, hydrates or esters thereof.

Certain of the sodium channel blockers, gabapentin and pregabalin may exist as optical isomers and the invention includes both the racemic mixtures of such optical isomers as well as the individual enantiomers that may be separated according to methods that are well know to those of ordinary skill in the art.

The invention disclosed herein is meant to encompass all pharmaceutically acceptable salts thereof of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass prodrugs of the disclosed compounds. Prodrugs are considered to be any covalently bonded carriers which release the active parent drug in vivo. Examples of prodrugs include esters or amides of compounds having hydroxyalkyl or aminoalkyl substituents, and these may be prepared by reacting such compounds with anhydrides such as succinic anhydride.

Some of the compounds disclosed herein may contain one or more asymmetric centers and may thus give rise to enantiomers, diastereomers, and other stereoisomeric forms. The present invention is also meant to encompass racemic mixtures, resolved forms mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The sodium channel blockers, gabapentin and pregabalin may be prepared using methods known to those skilled in the art.

Compositions within the scope of this invention include all compositions wherein the sodium channel blockers, gabapentin and/or pregabalin are contained in an amount which is effective to achieve its intended purpose. The amount of sodium channel blockers, gabapentin and/or pregabalin is preferably less than the amount needed when each compound is used alone as a single agent. While individual needs vary, determination of optimal ranges of effective amounts of each component is within the skill of the art. Typically, the sodium channel blockers may be administered to mammals, e.g. humans, orally at a dose of 0.1 to 10 mg/kg, or an equivalent amount of the pharmaceutically acceptable salt thereof, per day of the body weight of the mammal being treated. Gabapentin and/or pregabalin may be administered orally at a dose of about 50 to about 3200 mg/day, preferably about 150 to about 2400 mg/day, and more preferably 300 to 1800 mg/day, or an equivalent amount of the pharmaceutically acceptable salt thereof. For intramuscular injection, the dose is generally about one-half of the oral dose. Typically, pregabalin can be administered at lower doses than gabapentin.

With respect to the first agent, exemplary unit oral doses comprise:

For carbamazepine, from about 50 to about 1500 mg/day, preferably about 100 to about 800 mg/day, more preferably about 100 to about 600 mg/day, and most preferably about 100 to about 400 mg/day; or For lamotrigine, from about 50 to about 1200 mg/day, preferably 100 to about 600 mg/day, more preferably about 100 to about 450 mg/day, and most preferably about 100 to about 300 mg/day; or For Co 102862, from about 50 to about 1200 mg/day, preferably from about 200 to about 900 mg/day, more preferably from about 200 to about 750 mg/day, and most preferably from about 200 to about 600 mg/day Co 102862.

Additional useful unit oral doses for the first agent include:
from about 400 to about 800 mg/day carbamazepine,
from about 200 to about 600 mg/day lamotrigine
from about 350 to about 900 mg/day Co 102862.

With respect to the second agent, exemplary unit oral doses comprise:

from about 100 to about 3200 mg/day gabapentin, preferably about 100 to about 1800 mg/day gabapentin, and more preferably from about 150 to about 900 mg/day gabapentin; or from about 75 to about 900 mg/day pregabalin, preferably 75 to about 450 mg/day of pregabalin.

Another useful range is from about 300 to about 1800 mg/day of gabapentin. Another useful range is from about 150 to about 900 mg/day pregabalin.

The unit dose may be administered one or more times daily as one or more tablets.

In addition to administering the sodium channel blockers, gabapentin and pregabalin as a raw chemical, the compounds may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the sodium channel blockers, gabapentin and pregabalin. Acid addition salts are formed by mixing a solution of the particular compound with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the particular compound with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

In the practice of the present invention, the sodium channel blockers, gabapentin and pregabalin are preferably administered substantially simultaneously. By "substantially simultaneously" is intended to mean that the sodium channel blockers, gabapentin and/or pregabalin are administered in sequence or at the same time so long as effective blood levels of the sodium channel blockers, gabapentin and pregabalin are achieved at the same time. The first agent or the second agent can be administered first if sequential administration is chosen. It is preferred that the sodium channel blockers, gabapentin and pregabalin are administered as part of a single dosage form.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

Preferred sodium channel blocking properties exhibit an Ki of about 100 μM or less in the electrophysiological assay. Preferably, the sodium channel blockers exhibit an Ki of 10 μM or less. Most preferably, the sodium channel blockers exhibit an Ki of about 1.0 1 μM or less. The sodium channel blockers may be tested for their $Na^+$ channel blocking activity by the following electrophysiological and binding assays.

First Electrophysiological Assay:

Cell preparation: HEK-293 cells stably expressing the hSkM1 isoform of Na$^+$ channels (generous gift from Dr. A. L. George, Vanderbilt University Medical School) were cultured using standard techniques, as described previously (Verdoorn, T. A, et al., *Neuron* 4:919-928 (1990)). For electrophysiology, cells were plated onto 35 mm Petri dishes (pre-coated with poly-D-lysine) at a density of 1:40 on the day of re-seeding from confluent cultures. Cells are suitable for recordings for 2-3 days after plating.

Patch-clamp recordings of voltage-sensitive Na$^+$ currents: Whole-cell voltage-clamp recordings were made using conventional patch-clamp techniques (Hamill et al., *Pfluegers Arch*. 391:85-100 (1981)) with an Axopatch 200A amplifier (Axon Instruments, Foster City, Calif.). Recordings were made within 2-3 hours after neuron dissociation. The recording chamber was continuously superfused with the external solution (150 mM NaCl, 5.4 mM KCl, 1.8 mM CaCl$_2$, 1 mM MgCl$_2$, 10 mM HEPES, 10 mM glucose, pH 7.4 (NaOH)) at a speed of about 1 ml/min. Recording pipettes were pulled from thick-walled capillaries (WPI, Sarasota, Fla.) and fire-polished. The pipette resistances ranged from 1 to 3 MΩ when the pipettes were filled with internal solution containing (in mM): 110 CsF, 10 NaCl, 5 MgCl$_2$, 11 EGTA, 10 HEPES, pH adjusted to 7.4 with CsOH. Osmolality was set with a difference of 15-20 mmol/kg between external and internal solutions (lower inside the cell). Drugs and intervening wash-outs were applied through a linear array of flow pipes (Drummond Microcaps, 2-μl, 64-mm length). Compounds are dissolved in dimethylsulfoxide (DMSO) to make a 30 mM stock solution, which was subsequently diluted into the external solution to give final concentrations of 0.1-100 μM. At the highest (1%) concentration, DMSO inhibited the size of Na$^+$ current only slightly. Currents were recorded at room temperature (22-25° C.), filtered at 5 kHz with an active 8-pole Bessel filter (Frequency Devices, Haverhill, Mass.), digitized at 10-50-μs intervals, and stored using Digidata 1200 analog/digital interface with Pclamp6/Clampex software (Axon Instruments). Series resistance was cancelled typically by ~75% when necessary. The inhibitory potency of drugs was assessed by measuring reductions in the peak amplitude of Na$^+$ currents induced by increasing concentrations of compounds tested. Na$^+$ currents were elicited by stepping membrane voltage from holding potentials over the range −100 mV to −50 mV, to a pulse potential of −10 mV. The test pulse duration was 5-10 msec, repeated at a frequency ≦1 Hz. Concentration-inhibition curves were fitted with equation 1:

$$I/I_{control}=1/(1+([\text{compound}]/IC_{50})) \qquad \text{Eq. 1}$$

where $I_{control}$ is the maximal Na$^+$ current in the absence of antagonist, [compound] is the drug concentration, and IC$_{50}$ is the concentration of compound that produces half maximal inhibition.

Alternate Electrophysiological Assay:

Cell preparation: HEK-293 (NaIIA-B2) cell line stably expressing the rBIIA isoform of Na$^+$ channels is established in-house. The cells are cultured using standard techniques, as described previously (Verdoorn, T. A, et al., *Neuron* 4:919-928 (1990)). For electrophysiology, cells are plated onto poly-D-lysine pre-coated Cellware 35 mm Petri dishes (BIO-COAT, Becton Dickinson) at a density of ~10$^4$ cells/dish on the day of re-seeding from confluent cultures. Our experience has been that cells are suitable for recordings for 2-3 days after plating.

Patch-clamp recordings of voltage-sensitive Na$^+$ currents: Whole-cell voltage-clamp recordings are made using conventional patch-clamp techniques (Hamill et al., *Pfluegers Arch*. 391:85-100 (1981)) with an Axopatch 200A amplifier (Axon Instruments, Foster City, Calif.). The recording chamber is continuously superfused with the external solution (150 mM NaCl, 5.4 mM KCl, 1.8 mM CaCl$_2$, 1 mM MgCl$_2$, 10 mM HEPES, 10 mM glucose, pH 7.4 adjusted with NaOH, osmolality ~320 mmol/kg) at a speed of about 1 mL/min. Recording pipettes were pulled from the thick-walled capillaries (WPI, Sarasota, F l) and fire-polished. The pipette resistances range from 1 to 3 MΩ when the pipettes are filled with internal solution containing (in mM): 130 CsF, 20 NaCl, 2 MgCl$_2$, 10 EGTA, 10 HEPES, pH adjusted to 7.4 with CsOH, osmolality ~310 mmol/kg. Drugs and intervening wash-outs are applied through a linear array of flow pipes (Drummond Microcaps, 2 μL, 64-mm length). Compounds are dissolved in dimethylsulfoxide (DMSO) to make a 30 mM stock solution, which is subsequently diluted into the external solution to give final concentrations of 0.1-100 μM. At the highest (1%) concentration, DMSO inhibits the size of Na$^+$ current only slightly. Currents are recorded at room temperature (22-25° C.), filtered at 3 kHz with an active 8-pole Bessel filter (Frequency Devices, Haverhill, Mass.), digitized at 10-50 μs intervals, and stored using Digidata 1200 analog/digital interface with Pclamp6/Clampex software (Axon Instruments). Series resistance is cancelled typically by ~75% when necessary.

The following voltage pulse protocols A, B, C, and D are used to assess the potency and kinetics of inhibition of the Na$^+$ channels by the compounds (FIGS. 1A-1D).

Current-voltage relationship (IV-curve), protocol A (FIG. 1A), is used to report the voltage at which the maximal inward Na$^+$ current is achieved. This voltage is used throughout the experiment as testing voltage, V$_t$. The steady-state inactivation (or, availability) curve, protocol C (FIG. 1C), is used to get the voltage at which almost complete (≧95%) inactivation of Na$^+$ channels occurs; it serves as voltage for conditioning prepulse, V$_c$, throughout the experiment. Protocol B (FIG. 1B) reports how fast the channels recover from inactivation at hyperpolarized voltages. This permits us to set up the duration of the hyperpolarization gap which is used in measurement of the kinetics of binding of compounds to inactivated Na$^+$ channels (protocol D (FIG. 1D)). Channel repriming under control conditions is fast (≧90% recovery during first 5-10 ms). If a drug substantially retards the repriming process, then it becomes possible (protocol D) to accurately measure the kinetics of binding of the inhibitor to inactivated channels as well as the steady-state affinity (k$_+$ and K$_i$). To estimate k$_+$ values, the reduction in peak currents in successive trials with varying pre-pulse duration is plotted as a function of pre-pulse duration and the time constant (τ) measured by mono-exponential fit. A plot of 1/τ as a function of antagonist concentration then allows calculating of the macroscopic binding rates of the antagonists. To determine K$_i$ values the partial inhibition curves measured by fractional responses in steady-state are fitted with the logistic equation:

$$I/I_{control}=1/(1+([\text{antagonist}]/K_i)^p), \qquad \text{Eq. 2}$$

where $I_{control}$ is the maximal Na$^+$ current in the absence of antagonist, [antagonist] is the drug concentration, K$_i$ is the concentration of antagonist that produces half maximal inhibition, and p is the slope factor.

Binding Assay:

The ability of sodium channel blockers to modulate either site 1 or site 2 of the Na$^+$ channel may be determined following the procedures fully described in Yasushi, *J. Biol. Chem*.

261:6149-6152 (1986) and Creveling, *Mol. Pharmacol.* 23:350-358 (1983), respectively. Rat forebrain membranes were used as sources of $Na^+$ channel proteins. The binding assays are conducted in 130 μM choline chloride at 37° C. for 60-minute incubation with [$^3$H] saxitoxin and [$^3$H] batrachotoxin as radioligands for site 1 and site 2, respectively.

In vivo Pharmacology:

The compounds of the present invention may be tested for in vivo anticonvulsant activity after i.v., p.o. or i.p. injection using a number of anticonvulsant tests in mice, including the maximum electroshock seizure test (MES). Maximum electroshock seizures were induced in male NSA mice weighing between 15-20 g and male Sprague-Dawley rats weighing between 200-225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice were restrained by gripping the loose skin on their dorsal surface and saline-coated corneal electrodes were held lightly against the two corneae. Rats were allowed free movement on the bench top and ear-clip electrodes were used. Current was applied and animals were observed for a period of up to 30 sec for the occurrence of a tonic hindlimb extensor response. A tonic seizure was defined as a hindlimb extension in excess of 90 degrees from the plane of the body. Results were treated in a quantal manner.

The compounds may be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) were used in all experiments. Food was withdrawn on the day of experiment. Mice were placed in Plexiglass jars for at least 1 h to accommodate to the environment. Following the accommodation period mice were weighed and given either the compound of interest administered i.p. or p.o., or the appropriate volume of vehicle (10% Tween-80). Fifteen minutes after the i.p. dosing, and 30 min after the p.o. dosing mice were injected with formalin (20 μL of 5% formaldehyde solution in saline) into the dorsal surface of the right hind paw. Mice were transferred to the Plexiglass jars and monitored for the amount of time spent licking or biting the injected paw. Periods of licking and biting were recorded in 5 min intervals for 1 hr after the formalin injection. All experiments were done in a blinded manner during the light cycle. The early phase of the formalin response was measured as licking/biting between 0-5 min, and the late phase was measured from 15-50 min. Differences between vehicle and drug treated groups were analyzed by one-way analysis of variance (ANOVA). A P value$\leq$0.05 was considered significant. Having activity in blocking the acute and second phase of formalin-induced paw-licking activity, the compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200-225 g were anesthetized with halothane (1-3% in a mixture of 70% air and 30% oxygen) and their body temperature controlled during anesthesia through use of a homeothermic blanket. A 2-cm dorsal midline incision was then made at the L5 and L6 level and the para-vertibral muscle groups retracted bilaterally. L5 and L6 spinal nerves were then be exposed, isolated, and tightly ligated with 6-0 silk suture. A sham operation was performed exposing the contralateral L5 and L6 spinal nerves as a negative control.

Tactile Allodynia: Rats were transferred to an elevated testing cage with a wire mesh floor and allowed to acclimate for five to ten minutes. A series of Semmes-Weinstein monofilaments were applied to the plantar surface of the hindpaw to determine the animal's withdrawal threshold. The first filament used possessed a buckling weight of 9.1 gms (0.96 log value) and was applied up to five times to see if it elicited a withdrawal response. If the animal had a withdrawal response then the next lightest filament in the series would be applied up to five times to determine if it could elicit a response. This procedure was repeated with subsequent lesser filaments until there was no response and the lightest filament that elicited a response was recorded. If the animal did not have a withdrawal response from the initial 9.1 gm filament then subsequent filaments of increased weight were applied until a filament elicited a response and this filament was then recorded. For each animal, three measurements were made at every time point to produce an average withdrawal threshold determination. Tests were performed prior to and at 1, 2, and 24 hrs post drug administration. Tactile allodynia and mechanical hyperalgesia tests were conducted concurrently.

Mechanical Hyperalgesia: Rats were transferred to an elevated testing cage with a wire mesh floor and allowed to acclimate for five to ten minutes. A slightly blunted needle was touched to the plantar surface of the hindpaw causing a dimpling of the skin without penetrating the skin. Administration of the needle to control paws typically produced a quick flinching reaction, too short to be timed with a stopwatch and arbitrarily given a withdrawal time of 0.5 sec. The operated side paw of neuropathic animals exhibited an exaggerated withdrawal response to the blunted needle. A maximum withdrawal time of ten seconds was used as a cutoff time. Withdrawal times for both paws of the animals were measured three times at each time point with a five-minute recovery period between applications. The three measures were used to generate an average withdrawal time for each time point. Tactile allodynia and mechanical hyperalgesia tests were conducted concurrently.

The compounds may be tested for their neuroprotective activity after focal and global ischemia produced in rats or gerbils according to the procedures described in Buchan et al. (*Stroke*, Suppl. 148-152 (1993)) and Sheardown et al. (*Eur. J. Pharmacol.* 236:347-353 (1993)) and Graham et al. (*J. Pharmacol. Exp. Therap.* 276:1-4 (1996)).

The compounds may be tested for their neuroprotective activity after traumatic spinal cord injury according to the procedures described in Wrathall et. al. (*Exp. Neurology* 137: 119-126 (1996)) and Iwasaki et. al. (*J. Neuro Sci.* 134:21-25 (1995)).

The invention also relates to a kit for the treatment of chronic pain or convulsions comprising a carrier containing one or more containers one of which comprises a sodium channel blocker and another of which comprises at least one of gabapentin and pregabalin. Examples of such carriers include boxes, tubes and the like that are used to package pharmaceuticals. Examples of containers include bottles, jars, tubes and the like.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Coadministration of Co 102862 and Gabapentin

Figure 2:
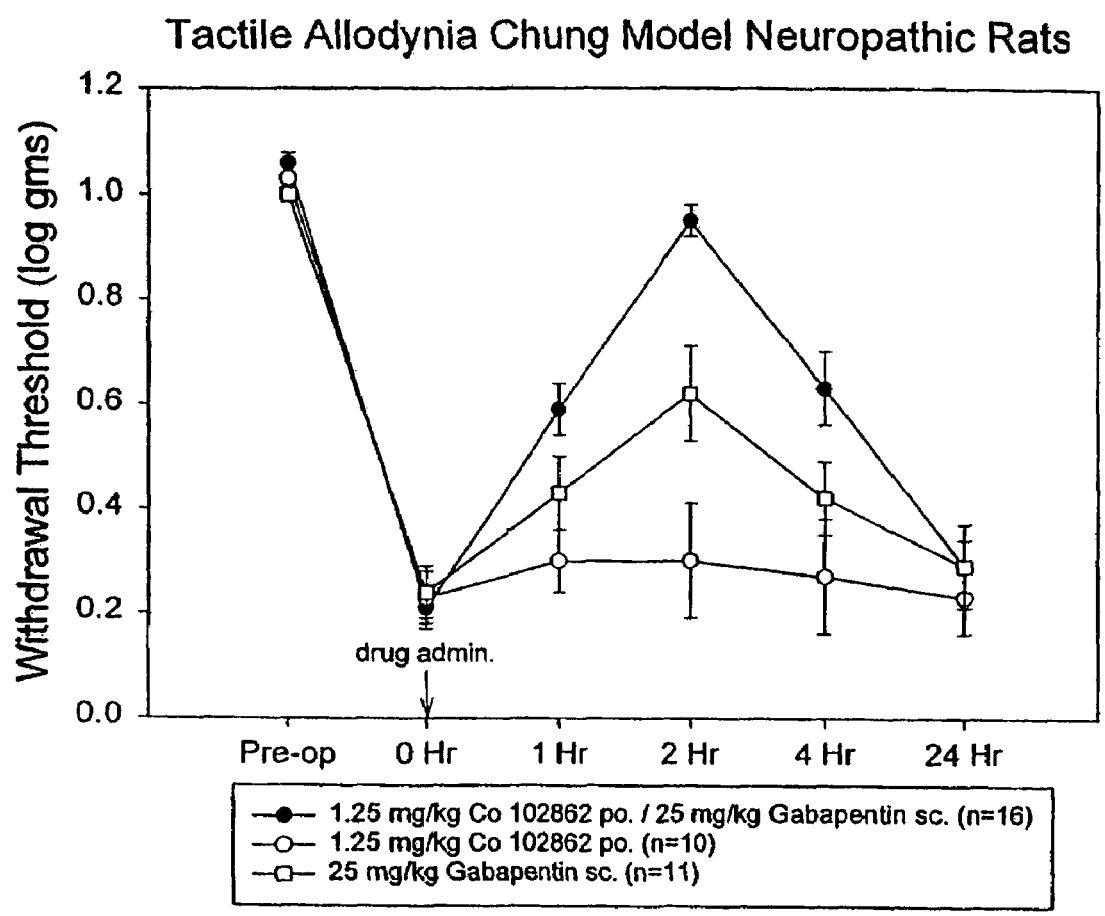
FIG. 2 depicts a graph showing the synergistic antiallodynic effect of gabapentin and the sodium channel blocker 4-(4'-fluoro-phenoxy)benzaldehyde semicarbazone (Co 102862) in the Chung model of neuropathic pain in rats (Kim and Chung, *Pain* 50: 355-363 (1992)).

The tactile antiallodynia effect of Co 102862 and gabapentin was tested alone or in combination in the Chung model of neuropathic rats. As shown in FIG. 2, rats that received 1.25 mg/kg Co 102862 p.o. showed moderate antiallodynia effect whereas 25 mg/kg gabapentin s.c. exhibited minimum or no effect when given alone. However, when both compounds were given together, a much greater withdrawal threshold was observed than if one were to add the effect of Co 102862 and gabapentin given individually. Thus, the combination of the two drugs has a synergistic effect. See FIG. 2.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating or ameliorating neuropathic pain, comprising administering to a patient in need thereof a first agent which is a semicarbazone represented by Formula I

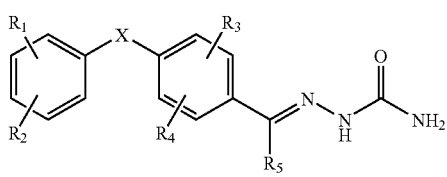

where $R_1$-$R_4$ are independently hydrogen, halogen, $C_{1-9}$ alkyl, $C_{3-9}$ cycloalkyl, cyano, $C_{1-9}$ alkoxy, or $C_{6-10}$ aryloxy; $R_5$ is hydrogen, $C_{1-9}$ alkyl, $C_{3-9}$ cycloalkyl, or $C_{6-10}$ aryl; and X is oxygen or sulfur; and a second agent selected from the group consisting of gabapentin, pregabalin, salts thereof and combinations thereof;

wherein said first agent and said second agent are present in synergistic amounts effective to treat or ameliorate neuropathic pain.

2. The method of claim 1, wherein said method is treating neuropathic pain.

3. The method of claim 1, wherein said neuropathic pain is due to cancer pain or idiopathic pain.

4. The method of claim 1, wherein said neuropathic pain is due to trigeminal neuralgia, acute herpetic neuralgia, acute postherpetic neuralgia, diabetic neuropathy, causalgia, brachial plexus avulsion, occipital neuralgia, reflex sympathetic dystrophy, fibromyalgia, or phantom limb pain.

5. The method of claim 4, wherein said neuropathic pain is due to trigeminal neuralgia.

6. The method of claim 4, wherein said neuropathic pain is due to diabetic neuropathy.

7. The method of claim 1, wherein said first agent and said second agent are administered substantially simultaneously.

8. The method of claim 1, wherein said first agent and said second agent are administered separately.

9. The method of claim 1, wherein said first agent and said second agent are administered as part of a single pharmaceutical preparation.

10. The method of claim 1, wherein said first agent and said second agent are administered intramuscularly, wherein the dose of said second agent is about 25 mg/day to about 1600 mg/day.

11. The method of claim 2, wherein said first agent is administered orally.

12. The method of claim 11, wherein said first agent is 4-(4'-flourophenoxy)-benzaldehyde semicarbazone.

13. The method of claim 12, wherein the amount of 4-(4'-fluorophenoxy)benzaldehyde semicarbazone is from about 50 to about 1200 mg/day.

14. The method of claim 13, wherein the amount of 4-(4'-fluorophenoxy)benzaldehyde semicarbazone is from about 200 to about 900 mg/day.

15. The method of claim 14, wherein the amount of 4-(4'-fluorophenoxy)benzaldehyde semicarbazone is from about 200 to about 750 mg/day.

16. The method of claim 15, wherein the amount of 4-(4'-fluorophenoxy)benzaldehyde semicarbazone is from about 200 to about 600 mg/day.

17. The method of claim 14, wherein the amount of 4-(4'-fluorophenoxy)benzaldehyde semicarbazone is from about 350 to about 900 mg/day.

18. The method of claim 2, wherein said second agent is administered orally.

19. The method of claim 18, wherein said second agent is gabapentin.

20. The method of claim 19, wherein the amount of gabapentin is from about 100 to about 3200 mg/day.

21. The method of claim 20, wherein the amount of gabapentin is from about 100 to about 1800 mg/day.

22. The method of claim 21, wherein the amount of gabapentin is from about 150 to about 900 mg/day.

23. The method of claim 21, wherein the amount of gabapentin is from about 300 to about 1800 mg/day.

24. The method of claim 18, wherein said second agent is pregabalin.

25. The method of claim 24, wherein the amount of pregabalin is from about 75 to about 900 mg/day.

26. The method of claim 25, wherein the amount of pregabalin is from 75 to about 450 mg/day.

27. The method of claim 25, wherein the amount of pregabalin is from about 150 to about 900 mg/day.

28. The method of claim 2, wherein said first agent is administered parenterally, subcutaneously, intravenously, intramuscularly, intraperitoneally, transdermally, or buccally.

29. The method of claim 2, wherein said second agent is administered parenterally, subcutaneously, intravenously, intramuscularly, intraperitoneally, transdermally, or buccally.

30. A method of treating or ameliorating neuropathic pain, comprising administering substantially simultaneously to a patient in need thereof a semicarbazone represented by Formula I

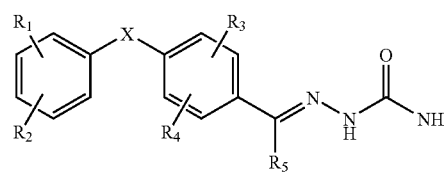

where $R_1$-$R_4$ are independently hydrogen, halogen, $C_{1-9}$ alkyl, $C_{3-9}$ cycloalkyl, cyano, $C_{1-9}$ alkoxy, or $C_{6-10}$ aryloxy; $R_5$ is hydrogen, $C_{1-9}$ alkyl, $C_{3-9}$ cycloalkyl, or $C_{6-10}$ aryl; and X is oxygen or sulfur; and at least one of gabapentin and pregabalin, wherein said semicarbazone and at least one of gabapentin and pregabalin are administered in synergistic amounts effective to treat or ameliorate neuropathic pain.

* * * * *

UNITED STATES PATENT AND TRADEMARK OFFICE
CERTIFICATE OF CORRECTION

| | | |
|---|---|---|
| PATENT NO. | : 7,393,872 B2 | Page 1 of 1 |
| APPLICATION NO. | : 10/644783 | |
| DATED | : July 1, 2008 | |
| INVENTOR(S) | : Nancy C. Lan | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (231) days.

Delete the phrase "by 231 days" and insert -- by 264 days --

Signed and Sealed this

Ninth Day of March, 2010

David J. Kappos
*Director of the United States Patent and Trademark Office*